United States Patent
Kovarik

(10) Patent No.: US 9,941,104 B2
(45) Date of Patent: Apr. 10, 2018

(54) SYSTEMS AND METHODS FOR DELIVERING LIQUID TO AN ION SOURCE

(71) Applicant: DH Technologies Development PTE Ltd., Singapore (SG)

(72) Inventor: Peter Kovarik, Markham (CA)

(73) Assignee: DH Technologies Development Pte. Ltd., Singapore (SG)

( * ) Notice: Subject to any disclaimer, the term of this patent is extended or adjusted under 35 U.S.C. 154(b) by 0 days.

(21) Appl. No.: 15/112,478

(22) PCT Filed: Nov. 18, 2014

(86) PCT No.: PCT/IB2014/002483
§ 371 (c)(1),
(2) Date: Jul. 19, 2016

(87) PCT Pub. No.: WO2015/110860
PCT Pub. Date: Jul. 30, 2015

(65) Prior Publication Data
US 2016/0336158 A1  Nov. 17, 2016

Related U.S. Application Data

(60) Provisional application No. 61/931,281, filed on Jan. 24, 2014.

(51) Int. Cl.
*H01J 49/00* (2006.01)
*H01J 49/04* (2006.01)
(Continued)

(52) U.S. Cl.
CPC .......... *H01J 49/0431* (2013.01); *G01N 30/04* (2013.01); *G01N 30/7233* (2013.01); *H01J 49/0009* (2013.01); *G01N 2030/047* (2013.01)

(58) Field of Classification Search
CPC .. H01J 49/00; H01J 49/02; H01J 49/04; H01J 49/0404; H01J 49/0409; H01J 49/0413;
(Continued)

(56) References Cited

U.S. PATENT DOCUMENTS 5,795,469 A   8/1998 Quinn et al.
6,100,522 A   8/2000 Chiang
(Continued)

FOREIGN PATENT DOCUMENTS

EP   0452930 A2   10/1991

OTHER PUBLICATIONS

Games et al., Continuous Flow Fast Atom Bombardment Liquid Chromatography/Mass Spectrometry: Studies Involving Conventional Bore Liquid Chromatography with Simultaneous Ultraviolet Detection, 1988, Biomedical and Environmental Mass Spectrometry, vol. 15, pp. 179-182.*

(Continued)

*Primary Examiner* — Jason McCormack

(57) ABSTRACT

Methods and systems for delivering a liquid sample to an ion source are provided herein: In various aspects, the methods and systems described herein can utilize the flow provided by an LC pump(s) to drive a calibration fluid to an ion source of a mass spectrometer system. In various aspects, methods and systems described herein can additionally or alternatively be placed upstream of an LC column for providing an elution gradient of a plurality of solvents, without requiring a plurality of pumps and/or separate mixing elements.

20 Claims, 8 Drawing Sheets

(51) Int. Cl.
*G01N 30/72* (2006.01)
*G01N 30/04* (2006.01)

(58) Field of Classification Search
CPC .. H01J 49/0431; H01J 49/0436; H01J 49/044;
H01J 49/0445; H01J 49/045; H01J
49/0454; G01N 30/72; G01N 30/7233
USPC ........................................ 250/281, 282, 288
See application file for complete search history.

(56) References Cited

U.S. PATENT DOCUMENTS

| | | | |
|---|---|---|---|
| 7,998,434 B2* | 8/2011 | Shaw | G01N 1/38 250/288 |
| 2006/0193748 A1* | 8/2006 | Tai | G01N 30/34 422/70 |
| 2007/0128078 A1* | 6/2007 | Sarrut | B01L 3/502707 422/400 |
| 2008/0296486 A1* | 12/2008 | Blanksby | H01J 49/0045 250/282 |
| 2010/0107742 A1 | 5/2010 | Liu et al. | |
| 2011/0065130 A1* | 3/2011 | Caprioli | G01N 33/574 435/7.23 |
| 2013/0219999 A1 | 8/2013 | Casey et al. | |
| 2014/0147921 A1* | 5/2014 | Chen | G01N 1/00 436/34 |
| 2015/0316516 A1* | 11/2015 | Albrecht, Jr. | G01N 30/20 73/61.56 |

OTHER PUBLICATIONS

International Search Report and Written Opinion for PCT/IB2014/002483 dated Feb. 23, 2015.

* cited by examiner

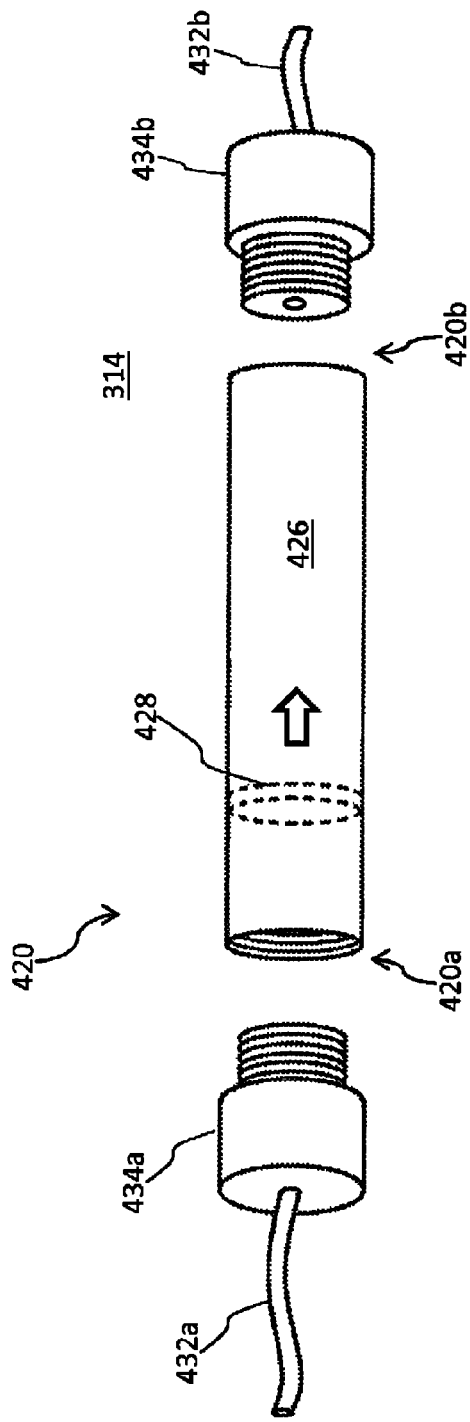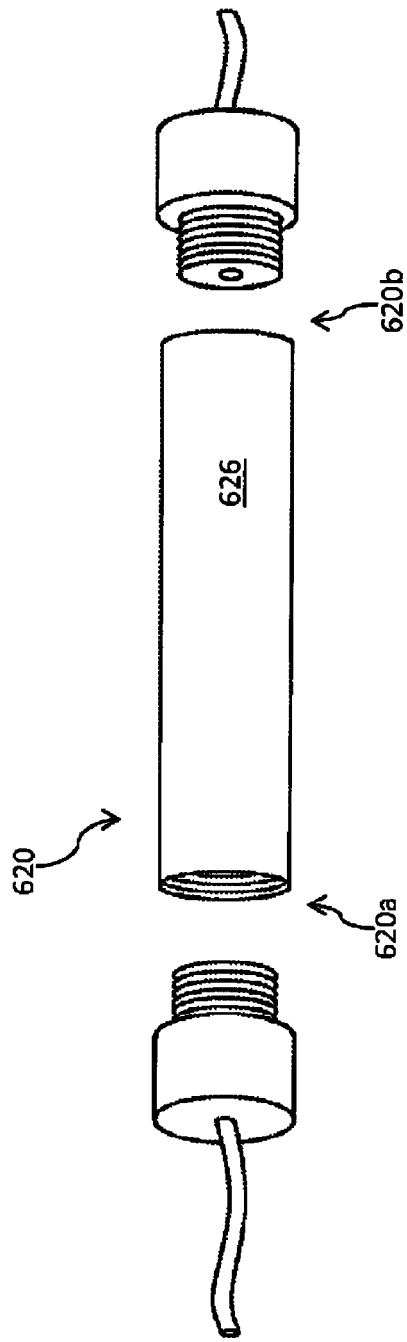
FIG. 4
FIG. 6

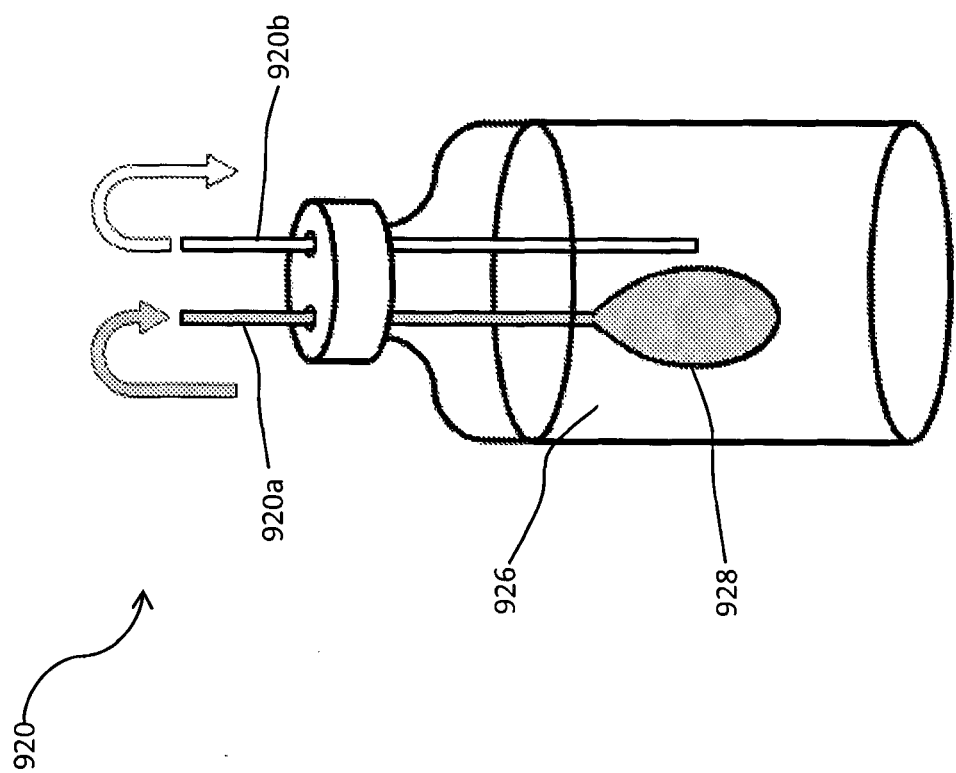

SYSTEMS AND METHODS FOR DELIVERING LIQUID TO AN ION SOURCE

RELATED APPLICATION

This application claims priority to U.S. provisional application No. 61/931,281, filed on Jan. 24, 2014, which is incorporated herein by reference in its entirety.

FIELD

The invention generally relates to mass spectrometry, and more particularly and without limitation, to methods and apparatus for delivering a liquid sample to an ion source.

INTRODUCTION

Mass spectrometry (MS) is an analytical technique for determining the elemental composition of test substances with both qualitative and quantitative applications. MS can be useful for identifying unknown compounds, determining the isotopic composition of elements in a molecule, determining the structure of a particular compound by observing its fragmentation, and quantifying the amount of a particular compound in a sample.

Due to the accuracy and sensitivity requirements for most MS applications, liquid samples are generally delivered to an ion source using highly accurate and precise (and thus expensive) pumps that generate a stable ion signal in a downstream mass analyzer. Further, in various applications, a plurality of such pumps are required. For example, as shown in the exemplary prior art system depicted in FIG. 1, liquid chromatography (LC) sample preparations often utilize separate pumps 130a,b for each of two different solvents 150a,b (i.e., solvents A and B) applied to the LC column 110. By way of example, the flow rate of each of the two pumps 130a,b can be programmed to change over the course of a sample run such that two solvents can be mixed (e.g., by mixer 104) to generate a mobile phase exhibiting a selected proportion of the solvents. Because chemical entities in the sample can be differentially affected by the composition of the mobile phase passing through the LC column 110, the user can generate chromatographic separation of the different chemical constituents based on the elution gradient.

Moreover, mass spectrometry systems also generally require frequent calibrations to ensure proper and/or optimal functioning. For example, one common calibration technique operates the mass spectrometer system at a "steady state" level such that the detected signal of a calibrant or compound of interest remains relatively constant. The mass spectrometer system can then be tuned by making adjustments to the various control parameters while monitoring the changes to the ion signal. Upon generation of a maximum signal, these ideal control parameter settings can then be "locked-in" for routine sample analysis of that compound. Similar processes are also used for verification and/or determination of mass assignment, for example, by interpolating the mass of an "unknown" compound based on the steady state signal of one or more compounds having a known molecular weight (e.g., calibrant). Precise delivery of the calibrant to the ion source is thus required to ensure the steady state operation.

Known strategies for delivering calibrant, however, can suffer from various disadvantages. For example, with reference to FIG. 1, direct infusion calibration techniques disconnect the sample source (e.g., taking LC column 110 offline by closing valve 102) and utilize a precise, low-volume pump 130c (e.g., syringe pump) to deliver calibration fluid 130c to the ion source 140. However, in this configuration, the ion source 140 is not operated under normal operating conditions (e.g., at the relatively high flow rates generated by the LC pump(s) 130a,b for driving a mobile phase through the LC column 110). If instead the LC pump(s) 130a,b are used to deliver the calibrant at a high flow rate, the LC pump(s) 130a,b can be contaminated and/or can result an unacceptable background signal.

Alternatively, in split "T" infusion techniques (e.g., valve 102 is open), a low flow calibrant pump 130c is operated to inject the calibrant into the high flow from the LC pump(s) at a "T" junction downstream from the LC column 110 such that the ion source is operated under normal, high flow settings. However, because the calibrant pump must work against the back pressure caused by the higher flow rate from the LC pumps 130a,b, an oscillating "steady state" signal can result. Another drawback of this technique lies in the decreased level of signal intensity as the calibrant is diluted by the LC flow.

Accordingly, there remains a need for improved and/or reduced-cost systems, methods, and devices for delivering a liquid sample and/or calibrant to an ion source of a mass spectrometer system.

SUMMARY

The present teachings generally relate to methods and systems for delivering a fluid to an ion source for the generation of ions and for their subsequent analysis by mass spectrometry. In accordance with various aspects of the applicant's teachings, methods and systems are described herein that provide a steady state flow of a calibration fluid, for example, utilizing the flow provided by the LC pump(s) to drive the calibration fluid from a reservoir of the calibration fluid (e.g., without a separate calibrant pump). In some aspects, for example, the methods and systems disclosed herein utilize a reservoir that can be placed in series with (or replace) an LC column to enable the delivery of the calibration fluid to the ion source operating under normal high-flow rate conditions. In various aspects, the fluid contained within the reservoir can be discharged therefrom at substantially the same volumetric flow rate of the fluid received at the inlet end of the reservoir, though the composition of the fluid exiting the reservoir may be different from that received thereby. In various aspects, apparatus in accordance with the present teachings can additionally or alternatively be placed upstream of an LC column to provide an elution gradient, of a plurality of solvents thereto, without requiring the use of a plurality of LC pumps, for example.

In accordance with various aspects, certain embodiments of the applicant's teachings relate to a system for delivering fluid to a mass spectrometry system that includes a pump and a reservoir comprising an inlet port configured to receive a first fluid driven by said pump and an outlet port configured to expel an output fluid of different composition than said first fluid, wherein the outlet port is configured to fluidly couple to an ion source of a mass spectrometry system.

In various aspects, the system defines a fluid flow pathway extending between the pump, an LC column, and the ion source, the reservoir being configured to removably couple to the fluid flow pathway. In some embodiments, the volumetric flow rate of the first fluid into the reservoir is substantially equal to the volumetric flow rate of the output fluid from the outlet port.

In some embodiments, the system can include a liquid chromatography (LC) column fluidly coupled to the pump and disposed between the pump and the reservoir. For example, the first fluid can be an eluent from the LC column and the output fluid can be a calibration fluid. In related aspects, the volumetric flow rate of the eluent into the inlet port can be substantially equal to the volumetric flow rate of the calibration fluid from the outlet port.

In some embodiments, the reservoir can be disposed between the pump and the LC column. In such embodiments, for example, the first fluid can be a first LC solvent and the output fluid can be a second LC solvent. In some aspects, the reservoir is configured to contain a second fluid having a different composition than the first fluid and the output fluid, wherein the first fluid comprises a first LC solvent and the second fluid comprises a second LC solvent, and wherein the output fluid comprises a mixture of the first and second LC solvents. In related aspects, the relative amount of the first LC solvent in the output fluid can increase over time. For example, the output fluid can be configured to provide a gradient elution of the LC column.

In some aspects, the reservoir can be configured to contain a second fluid having a different composition than the first fluid and the output fluid, the first and second fluids being mixed within the reservoir so as to generate the output fluid.

In various aspects, the reservoir can include a liquid impermeable partition disposed between the inlet port and the outlet port. In some aspects, the partition can be movable along the axis of the reservoir. A pressure exerted on an upstream surface of the partition by the first fluid, for example, can be effective to move the partition axially within the reservoir. In some aspects, the partition can comprise an expandable bladder. By way of example, a pressure exerted on the bladder by the first fluid can be effective to expand the bladder.

In some aspects, the system can include a fluid flow pathway extending between the pump, the LC column, and the ion source, the reservoir being disposed in the fluid flow pathway. In related aspects, for example, the system can also include a second reservoir disposed downstream of the first reservoir in the fluid flow pathway, wherein an inlet port of the second reservoir is configured to receive the output fluid of the first reservoir. In other aspects, the system can further include a bypass conduit extending from a first end coupled to the fluid flow pathway upstream from the reservoir to a second end coupled to the fluid flow pathway downstream from the reservoir. In some aspects, at least one valve can be disposed in the fluid flow pathway to control fluid flow into at least one of the bypass conduit and the reservoir.

In accordance with various aspects, certain embodiments of the applicant's teachings relate to method for delivering fluid to a mass spectrometry system, the method including operating a pump to introduce a first fluid into an inlet port of a reservoir containing a second fluid different than said first fluid, discharging an output fluid from an outlet port of the reservoir, wherein said output fluid is of a different composition from said first fluid, and delivering a sample fluid to be ionized to an ion source of a mass spectrometer. In some aspects, for example, operation of said pump is effective to introduce the first fluid into the inlet port of the reservoir, discharge the output fluid from the outlet port of the reservoir, and deliver the sample fluid to the ion source.

In various aspects, the pump, an LC column, the reservoir, and the ion source can be fluidly coupled via a fluid flow pathway. In some aspects, the method can include bypassing the reservoir. For example, the first fluid flow can be diverted from the reservoir (e.g., by actuating a valve disposed upstream from the reservoir). In related aspects, the method can also include decoupling the bypassed reservoir from a conduit defining the fluid flow pathway and/or refilling the bypassed reservoir.

In some embodiments, the method can comprise operating the pump to introduce a solvent into a liquid chromatography (LC) column. In some aspects, the LC column can be disposed between the pump and the reservoir. In related aspects, the second fluid, said output fluid, and said sample fluid comprise a calibration fluid. For example, the first fluid can comprise an eluent from the LC column. In some aspects, the volumetric flow rate of the first fluid into the inlet port can be substantially equal to the volumetric flow rate of the calibration fluid from the outlet port.

In some embodiments, the reservoir can be disposed between the pump and the LC column. For example, the first fluid can comprise a first LC solvent and the second fluid can comprise a second LC solvent, wherein the solvent introduced into the LC column comprises the output fluid discharged from the reservoir. In some aspects, the output fluid discharged from the reservoir consists of the second LC solvent during a first time duration. In some related aspects, the output fluid discharged from the reservoir comprises a mixture of the first and second LC solvents during a second time duration after the first time duration. For example, the relative amount of the first LC solvent in the output fluid can increase during the second time duration.

In accordance with various aspects, certain embodiments of the applicant's teachings relate to a mass spectrometer system that includes a pump, a liquid chromatography (LC) column fluidly coupled to the pump, and a reservoir comprising an inlet port configured to receive a first fluid driven by said pump and an outlet port configured to expel an output fluid of different composition than said first fluid. The exemplary system also includes an ion source fluidly coupled to the outlet port and a mass analyzer for analyzing ions generated by the ion source.

These and other features of the applicant's teachings are set forth herein.

BRIEF DESCRIPTION OF THE DRAWINGS

The skilled person in the art will understand that the drawings, described below, are for illustration purposes only. The drawings are not intended to limit the scope of the applicant's teachings in any way.

FIG. 4, in a schematic diagram, illustrates in detail an exemplary reservoir in accordance with various aspects of the applicant's teaching.

FIG. 6, in a schematic diagram, illustrates in detail another exemplary reservoir in accordance with various aspects of the applicant's teachings.

FIG. 9, in a schematic diagram, illustrates another exemplary reservoir in accordance with various aspects of the applicant's teachings.

DETAILED DESCRIPTION

Figure 1:
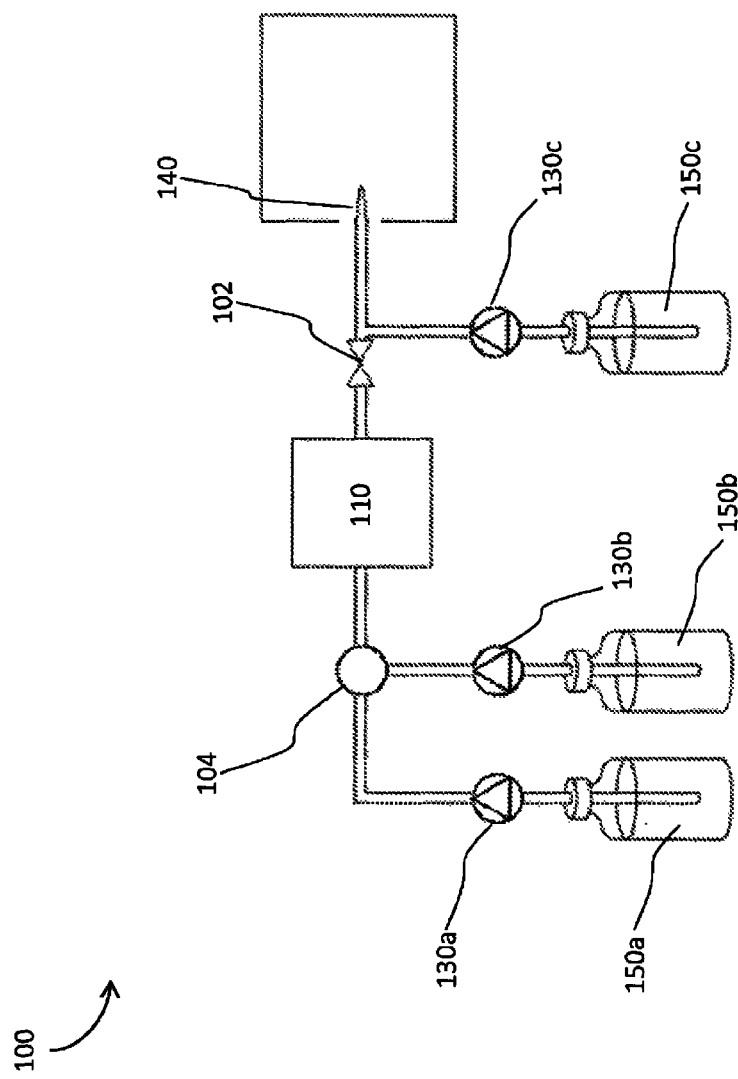
FIG. 1, in a schematic diagram, illustrates a known LC/MS system having multiple HPLC pumps and a separate calibration pump disposed downstream from the LC column.

It will be appreciated that for clarity, the following discussion will explicate various aspects of embodiments of the applicant's teachings, while omitting certain specific details wherever convenient or appropriate to do so. For example, discussion of like or analogous features in alternative embodiments may be somewhat abbreviated. Well-known ideas or concepts may also for brevity not be discussed in any great detail. The skilled person will recognize that some embodiments of the applicant's teachings may not require certain of the specifically described details in every implementation, which are set forth herein only to provide a thorough understanding of the embodiments. Similarly it will be apparent that the described embodiments may be susceptible to alteration or variation according to common general knowledge without departing from the scope of the disclosure. The following detailed description of embodiments is not to be regarded as limiting the scope of the applicant's teachings in any manner. As used herein, the terms "about" and "substantially equal" refer to variations in a numerical quantity that can occur, for example, through measuring or handling procedures in the real world; through inadvertent error in these procedures; through differences in the manufacture, source, or purity of compositions or reagents; and the like. Typically, the terms "about" and "substantially equal" as used herein means greater or lesser than the value or range of values stated by 1/10 of the stated values, e.g., ±10%. For instance, a concentration value of about 30% or substantially equal to 30% can mean a concentration between 27% and 33%. The terms also refer to variations that would be recognized by one skilled in the art as being equivalent so long as such variations do not encompass known values practiced by the prior art.

In accordance with various aspects of the applicant's teachings, the methods and systems described herein can reduce the number of pumps for transporting fluids of different compositions (e.g., sample and calibrant, solvents mixed for the mobile phase of chromatographic separation) upstream of an ion source in a system for mass spectrometry. In some aspects, a steady state flow of a calibration fluid can be provided by utilizing the flow provided by an LC pump(s) to drive the calibration fluid (e.g., without a separate calibrant pump). For example, various aspects of the methods and systems in accordance with the present teachings utilize a reservoir of a calibration fluid that can be placed downstream from an LC pump (e.g., in series with an LC column or temporarily replacing the LC column) to enable the delivery of the calibration fluid to the ion source operating under normal high-flow conditions. In various aspects, the fluid contained within the reservoir can be discharged therefrom at substantially the same volumetric flow rate of the fluid received by the reservoir, though the composition of the fluid discharged by the reservoir may be different from that received thereby. In various aspects, apparatus in accordance with the present teachings can additionally or alternatively be placed upstream of an LC column for providing an elution gradient of a plurality of solvents, without requiring a plurality of pumps and/or separate mixing elements.

Figure 2:
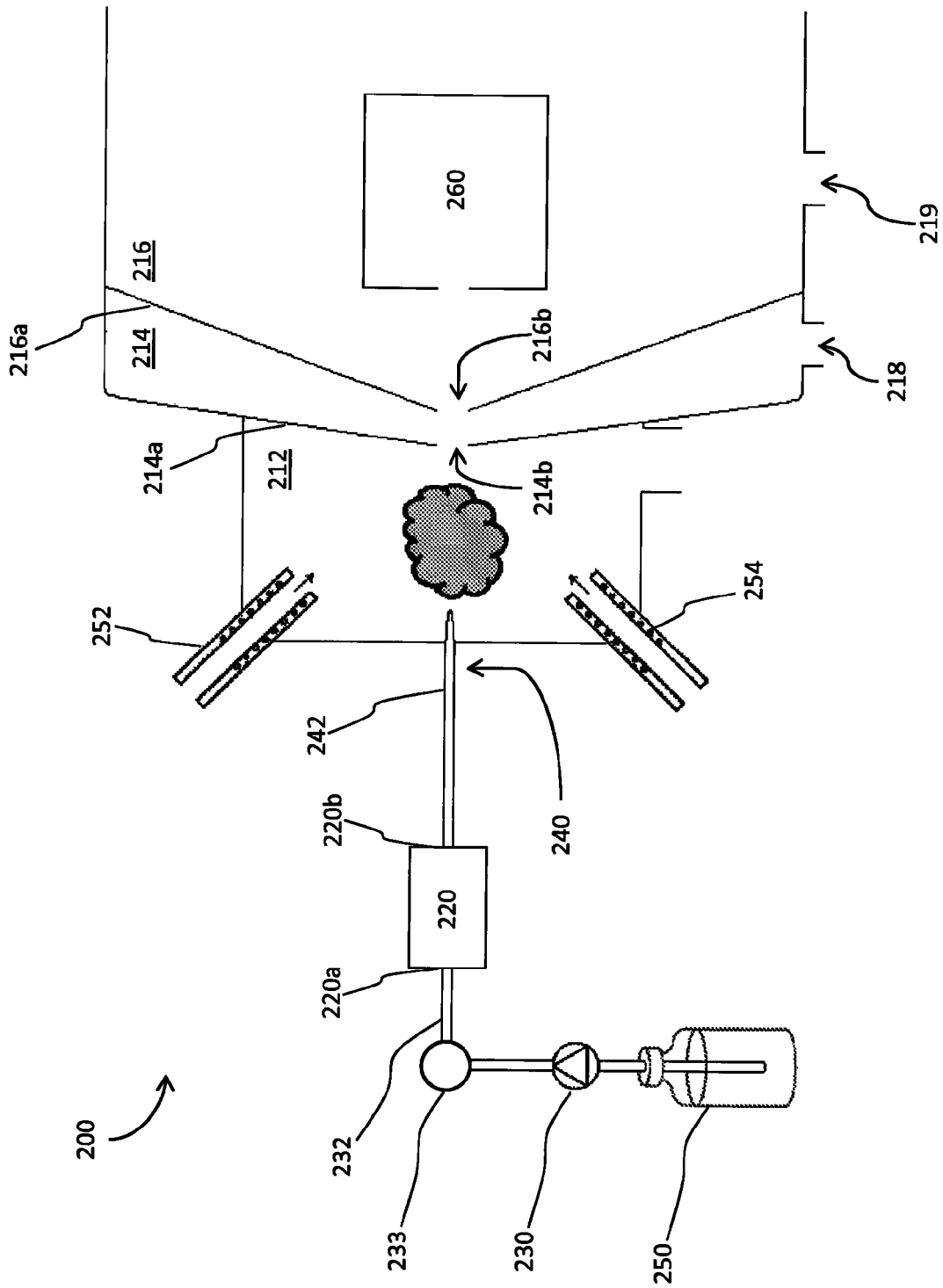
FIG. 2, in a schematic diagram, illustrates an exemplary mass spectrometry system, the system having an exemplary reservoir containing a calibrant in accordance with various aspects of the applicant's teaching.

FIG. 2 schematically depicts an exemplary embodiment of a mass spectrometer system 200 in accordance with various aspects of the applicant's teachings. As shown in FIG. 2, the exemplary mass spectrometer system 200 generally includes a reservoir 220 containing a fluid to be ionized (e.g., a calibration fluid), a pump 230, an ion source 240, and a mass analyzer 260 for the downstream processing of sample ions. As will be discussed in more detail below, the pump 230 generally provides a flow of a driving fluid (e.g., from fluid source 250) that is delivered to the reservoir 220 through one or more conduits 232 (e.g., channels, tubing, pipes, capillary tubes, etc.). In accordance with various aspects of the present teachings, the fluid reservoir 220 can receive the driving fluid at its inlet end (e.g., inlet port 220a) and discharge from its outlet end (e.g., outlet port 220b) fluid contained within the reservoir 220 for delivery to the ion source 240, which discharges the fluid into the ionization chamber 212. As will be discussed in detail below, in various aspects of the present teachings, the fluid discharged by the fluid reservoir 220 can have substantially the same volumetric flow rate as the driving fluid received by the fluid reservoir 220, though the composition of the fluid initially contained within the reservoir 220 and/or discharged therefrom can have a different composition than the driving fluid.

In the depicted embodiment, the ionization chamber 212 can be maintained at an atmospheric pressure, though in some embodiments, the ionization chamber 212 can be evacuated to a pressure lower than atmospheric pressure. The ionization chamber 212, within which analytes in the liquid sample are ionized, is separated from a gas curtain chamber 214 by a plate 214a having a curtain plate aperture 214b. As shown, a vacuum chamber 216, which houses the mass analyzer 260, is separated from the curtain chamber 214 by a plate 216a having a vacuum chamber sampling orifice 216b. The curtain chamber 214 and vacuum chamber 216 can be maintained at selected pressures, for example, by introducing curtain gas through port 218 and/or by evacuation through one or more vacuum pump ports 219.

The ion source 240 can also have a variety of configurations but is generally configured to generate ions from a liquid sample. By way of example, the ion source 240 can generate sample ions from at least one of a fluid containing a transient sample injected into the fluid by a sample injector 233, a fluid containing an analyte(s) of interest stored within the fluid source 250, and/or the fluid discharged from reservoir 220. In the exemplary embodiment depicted in FIG. 2, an outlet conduit 242 (e.g., a sample probe), which can comprise a capillary, for example, terminates in an outlet end that at least partially extends into the ionization chamber 212 and discharges a fluid therein. As will be appreciated by a person skilled in the art in light of the present teachings, the outlet end of the outlet conduit 242 can, atomize, aerosolize, nebulize, or otherwise discharge (e.g., spray with a nozzle) the liquid sample into the ionization chamber 212 to form a sample plume comprised a plurality of micro-droplets generally directed toward (e.g., adjacent to) the curtain plate aperture 214b and vacuum chamber sampling orifice 216b. As is known in the art, analyte molecules contained within the micro-droplets can be ionized (i.e., charged) by the ion source 240, for example, as the sample plume is generated. By way of non-limiting example, the outlet end of the outlet conduit 242 can be made of a conductive material and electrically coupled to a pole of a voltage source (not shown). Micro-droplets contained within the sample plume can thus be charged by the voltage applied to the outlet end such that as the liquid (e.g., solvent) within the droplets evaporate during desolvation in the ionization chamber 12, bare charged analyte ions are released and drawn toward and through the apertures 214b, 216b and focused (e.g., via one or more ion lens) into the mass analyzer 260. It should be appreciated that any number of different ionization techniques known in the art can be utilized as the ion source 240 in accord with the present teachings. By way of non-limiting example, the ion source 240 can be an electrospray ionization device, a nebulizer assisted electrospray device, a chemical ionization device, a nebulizer assisted atomization device, an inductively coupled plasma (ICP) ion source, a matrix-assisted laser desorption/ionization (MALDI) ion device, a glow discharge ion device, an electron impact ion device, a chemical ionization device, a thermospray ionization device, a sonic spray ionization device, or a photoionization device, among others.

As shown in FIG. 2, the exemplary mass spectrometer system 200 optionally includes one or more heaters 252 for heating the ionization chamber 212 to promote desolvation of the liquid (e.g., solvent) within the sample plume. By way of example, the heater(s) 252 can provide a flow of heated gas to the ionization chamber 212 (e.g., heated by heating elements 254). In some aspects, the heater(s) 252 can be effective to raise the temperature of the ionization chamber to a temperature in a range of from about 100° C. to about 800° C. The heater(s) 252 and the ion source 240 can have a variety of configurations, but are generally positioned relative to one another and to the apertures 214b, 216b such that the heated gas flow directs the sample plume to the proximity of the apertures 214b, 216b. In some embodiments, the ion source 240 and the heater(s) 252 can be positioned relative to one another such that the heated gas stream intersects the sample plume generated by the ion source 240 at a region within the ionization chamber 212 between the outlet end of the outlet conduit 242 and the aperture 214a.

It will be appreciated by a person skilled in the art that the mass spectrometer system 200 can optionally include a source of pressurized gas (e.g. nitrogen, air, or noble gas) that supplies a high velocity nebulizing gas flow which surrounds the outlet end of the outlet conduit 242 and interacts with the fluid discharged therefrom to enhance the formation of the sample plume, e.g., via the interaction of the high speed nebulizing flow and jet of liquid sample. The nebulizer gas can be supplied at a variety of flow rates, for example, in a range from about 0.1 L/min to about 20 L/min.

It will also be appreciated by a person skilled in the art and in light of the teachings herein that the mass analyzer 260 can have a variety of configurations. Generally, the mass analyzer 260 is configured to process (e.g., filter, sort, dissociate, detect, etc.) sample ions generated by the ion source 240. By way of non-limiting example, the mass analyzer 260 can be a triple quadrupole mass spectrometer, or any other mass analyzer known in the art and modified in accordance with the teachings herein. Additionally, the mass spectrometry system 200 can comprise a detector that can detect the ions which pass through the analyzer 260 and can, for example, supply a signal indicative of the number of ions per second which are detected.

As noted above, the exemplary mass spectrometer system 200 also includes a pump(s) 230 for delivering a driving fluid from a fluid source 250 to the reservoir 220 through one or more conduits 232. That is, the pump 230 can be fluidly connected directly or indirectly (e.g., through one or more elements disposed in the fluid pathway) to the inlet port 220a of the reservoir 220 to generate an input flow into the reservoir 220. In some aspects, for example, the system 200 can utilize multiple pumps 230 such as those utilized in a HPLC system, whose outputs are merged into the inlet port 220a of the reservoir 220. Moreover, as otherwise discussed herein, the flow generated by the pump(s) 230 can be effective to discharge fluid contained within the reservoir 220, for example, at substantially the same volumetric flow rate as the flow entering inlet port 220a of the reservoir. It should be appreciated in light of the present disclosure that pumps for use in the methods and systems described herein can have a variety of configurations and can generally comprise any pump mechanism known in the art and modified in accord with the present teachings that is configured to transport fluid through the conduits 232 and deliver fluid to the reservoir 220 and the ion source 240. By way of non-limiting example, syringe pumps, LC pumps, positive displacement pumps such as rotary, gear, plunger, piston, peristaltic, diaphragm pump, and other pumps such as gravity, impulse and centrifugal pumps can be used to pump the driving liquid directly or indirectly into the reservoir 220. Pump mechanisms for use in the systems and methods described herein can be configured to generate volumetric flow rates between about 10 μL per minute to about 20 mL per minute, by way of non-limiting examples.

As will be appreciated by a person skilled in the art in light of the present teachings, the pump 230 can be fluidly coupled to and receive a driving fluid from a variety of fluid sources 250. As shown in FIG. 2, for example, the source 250 of the driving fluid can comprise a vessel containing the driving fluid from which the pump 230 can draw or expel the driving fluid into the conduit 232. In some aspects, the driving fluid can comprise a liquid sample that is to be analyzed by the mass spectrometer system 200 (e.g., a reservoir of the sample to be analyzed or a reservoir of a blank liquid carrier and an input port through which the sample can be injected, for example, via a sample injector 233 such as an auto-sampler). Alternatively, the source 250 and pump 230 of the driving fluid can comprise a pump system and its mobile phase container(s) used in the liquid chromatography (LC) separation of sample components. By way of example, the pump 230 can be one or more HPLC pumps used to operate an LC column (not shown in FIG. 2) disposed between the pump 230 and the reservoir 220 such that the driving fluid for the pump can be the fluid output from the LC column. In some aspects, for example, the LC column can be temporarily replaced by the reservoir 220. In some aspects, the driving fluid can be a blank solution that enables the pump 230 to be run under the normal operating conditions used to deliver a liquid sample to the ion source 240 for ionization and mass spectrometric analysis. In some aspects, the reservoir 220 can be removed from or by-passed by the conduit 232, for example, when LC separation is taking place, as otherwise discussed herein.

In accordance with various aspects of the present teachings, the fluid reservoir 220 can receive the driving fluid flow at its inlet port 220a so as to discharge from its outlet port 220b fluid contained within the reservoir 220 for delivery (directly or indirectly) to the ion source 240. For example, as shown in FIG. 2, the outlet end 220b of the reservoir 220 can be directly coupled into the outlet conduit 242 of the ion source 220. The reservoir 220 can have a variety of configurations, but can be configured such that the volumetric flow rate of the fluid discharged by the fluid reservoir 220 can be substantially equal to the volumetric flow rate of the driving fluid received by the fluid reservoir 220, as will be described in detail below. Moreover, in exemplary aspects, the fluid reservoir 220 can contain and/or be filled with a different fluid than the fluid delivered thereto by the pump 230 such that the input fluid and output fluid of the reservoir 220 can differ in composition. By way of example, as shown in FIG. 2, the reservoir 220 can contain a calibration fluid that can be used to calibrate the mass spectrometer and/or verify its operation, while the fluid source 250 can provide a driving fluid to the inlet port 220a comprising a different fluid (e.g., a sample fluid or blank solution). Accordingly, though the volumetric flow rates of driving fluid into the inlet port 220a and fluid out of the outlet port 220b can be substantially equal, the composition between the fluids can vary. By way of example, in some aspects, the driving fluid can be segregated within the reservoir 220 from the fluid initially contained therein such that the outlet fluid wholly consists of the fluid initially contained within the reservoir 220. For example, in an embodiment in which the fluid initially contained within the reservoir comprises a calibration fluid, operation of the system to generate a flow of a driving fluid into the inlet port 220a of the reservoir 220 can be effective to drive the calibration fluid out of the reservoir 220 (and into the ion source 240, for example, to enable calibration of the mass spectrometer system 200). Alternatively, in some aspects, the driving fluid and the fluid initially contained within the reservoir 220 can be mixed therein such that the outlet fluid comprises a mixture of the driving fluid and the fluid initially contained within the reservoir 220.

Though the fluid discharged from the outlet end 220b of the reservoir 220 is shown as being directly coupled into the outlet conduit 242 of the ion source 220 in FIG. 2, it will be appreciated that the fluid discharged from the reservoir can be indirectly delivered to an ion source through one or more additional conduits or sample processing elements (e.g., an LC column). For example, with reference now to FIG. 3, another exemplary mass spectrometer system 300 in accordance with the present teachings is depicted. The system 300 is similar to that depicted in FIG. 2, but differs in that the fluid flow pathway between the pump 330 and the ion source 340 additionally includes an LC column 310 disposed between the reservoir 320 and the ion source 340. That is, the reservoir 320, which receives at its inlet port 320a a driving fluid via conduit 332a, discharges from its outlet port 320b into conduit 332b fluid to be run through the LC column 310 prior to being delivered to the ion source 340. Though the pump 350 can comprise any pumping mechanism known in the art and modified in accordance with the present teachings as discussed above, in one exemplary embodiment the pump 350 is a pumping mechanism configured to drive a mobile phase through the LC column 310 (via the reservoir 320) to effect chromatographic separation in the LC column 310. By way of example, the pump 350 can be any pump configured for low-pressure LC or relatively high-pressure HPLC and modified in accordance with the present teachings. Optionally, in some aspects, a sample injector 333 (e.g., an auto-sampler) can also be disposed upstream of the LC column 310 such that small volumes of a liquid sample can be injected into the fluid introduced into the LC column 310 at specified times during an extended sample run, for example.

Figure 3:
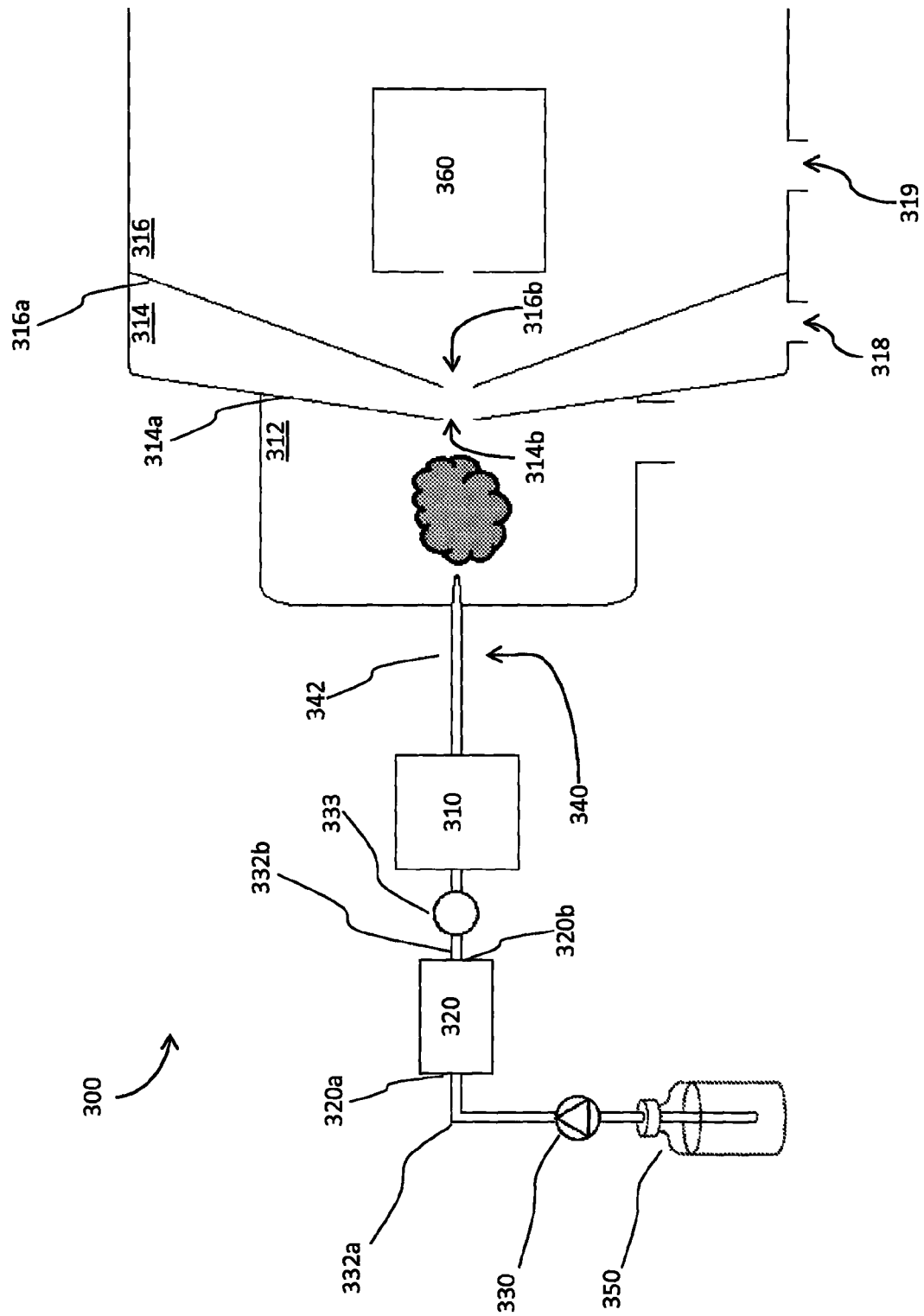
FIG. 3, in a schematic diagram, illustrates another exemplary mass spectrometry system, the system having an exemplary reservoir in accordance with various aspects of the applicant's teachings for generating the mobile phase to be run through an LC column.

As above, the reservoir 320 can contain and/or be filled with a different fluid than the fluid delivered thereto by the pump 330 such that the input fluid and output fluid of the reservoir 320 differ in composition. By way of example, as shown in FIG. 3, the reservoir 320 can contain a solvent used in LC separation, while the fluid source 350 can provide a driving fluid to the inlet port 320a comprising a different fluid (e.g., a blank solution or a second solvent also used to effect chromatographic separation). Accordingly, though the volumetric flow rates of the driving fluid into the inlet port 320a and the fluid discharged from the outlet port 320b can be substantially equal, the composition between the fluids can differ. By way of example, in some aspects, the driving fluid can be segregated within the reservoir 320 from the fluid initially contained therein such that the outlet fluid wholly consists of the LC solvent initially contained within the reservoir 320. Alternatively, as will be discussed in detail below, in some aspects the driving fluid and the fluid initially contained within the reservoir 220 can be mixed therein such that the outlet fluid comprises a mixture of the driving fluid and the fluid initially contained within the reservoir 320. For example, in an embodiment in which the reservoir 320 initially contains a solvent A that can be driven therefrom by input of solvent A into the inlet end 320a, the output fluid can comprise a mix of solvents A and B. Moreover, the proportions of solvent A to solvent B can vary over time as the driving fluid is continually introduced into the reservoir 320 such that the output fluid comprises a time-dependent concentration gradient. For example, the fluid initially discharged from the reservoir 320 may wholly consist of solvent A, but as solvent B is introduced into the reservoir 320 and the solvents mix therein, the percentage of the output fluid made up by solvent B can increase over time from about 0% to about 100%.

Reservoirs for use in the exemplary systems 200 and 300 described above with reference to FIGS. 2 and 3 can have a variety of configurations but generally comprise a fluid containing chamber. For example, with reference now to FIG. 4, one exemplary embodiment of a reservoir 420 in accordance with various aspects of the present teachings is depicted in detail. As shown in FIG. 4, the reservoir 420 generally extends from an upstream, inlet port 420a to a downstream, outlet port 420b defining the fluid containing chamber 426 therebetween (e.g., along a direction of fluid flow). In various aspects, the fluid containing chamber 426 can be configured to couple to a fluid flow pathway, which extends for example between a pump and an ion source as discussed above, in any suitable manner, such as, for example, using any one of known fluid-tight couplings (e.g., by an adhesive, solvent or non-solvent bonding, welding, mechanical interlock, interference fit, etc.). By way of example, the exemplary reservoir 420 can be configured to couple to the inlet conduit 432a and the outlet conduit 432b via fluidic coupling elements 434a,b respectively. For example, as shown in FIG. 4, the inlet end of the reservoir 420 can comprise a threaded bore configured to receive a corresponding threaded fitting 434a coupled to the downstream end of inlet conduit 432a (e.g., a standard 10-32⅟₁₆" fitting). As shown, the outlet end of the reservoir 420 can similarly comprise a threaded bore which can receive a corresponding threaded fitting 434b that is coupled to the upstream end of the outlet conduit 432b. It will be appreciated by a person skilled in the art in light of the present teachings, however, that the coupling elements 434a,b need not be identical to one another. By way of example, in an exemplary embodiment in which the reservoir 420 can be removably coupled in series to the fluid flow pathway, the fluidic coupling elements 434a,b can also be configured to form a fluid-tight connection to one another when the reservoir 420 is removed (e.g., disconnected) from the fluid flow pathway. As such, though both fluidic coupling elements 434a,b are depicted in FIG. 4 as being male elements received within the female threaded bores of the reservoir, in one exemplary embodiment, one of the coupling elements 434a,b can be female and the other male such that these coupling elements 434a,b can be fluidly coupled to one another if the reservoir 420 is removed from the fluid flow pathway.

It will be appreciated that the fluid-containing chamber 426 of the reservoir 420 can be sized to contain a range of fluid volumes. By way of non-limiting example, reservoirs in accordance with the present teachings can be configured to contain various volumetric capacities depending, for example, on the application and/or location of the reservoir within the fluid flow pathway. In embodiments in which the reservoir is configured to dispense calibration fluid under the action of a low-volume pump for delivering low volumetric flows of a sample to the ion source (e.g., flow rates in a range of about 10 μL to about 1000 μL per minute), the reservoir can have a volumetric capacity ranging only up to a few mLs, for example. In applications in which the reservoir 420 is disposed upstream of an LC column and the reservoir 420 contains a portion of the mobile phase to be applied thereto, for example, the chamber can have a greater volumetric capacity (e.g., up to about 250 mLs).

In various aspects, the cross-sectional area of the chamber 426 of the reservoir 420 can differ relative to the cross-sectional area of the input and/or output conduits (and indeed the majority of the fluid flow pathway). By way of example, the ratio of the cross-sectional area of the chamber 426 to the inner diameter of the inlet conduits and outlet conduits can be in a range from about 0.01 to about 1000. As shown in FIG. 4, for example, the cross-sectional area of the chamber 426 can in some embodiments be greater than the cross-sectional area of the conduits 432a,b that supply the driving fluid and receive the discharged fluid so as to accommodate a volume of fluid in the reservoir.

As shown in FIG. 4, the exemplary reservoir 420 additionally includes a partition 428 for segregating the fluid initially contained in the chamber 426 from that fluid received in the inlet port 420a. The partition 428 can have a variety of configurations but generally prevents the input fluid (e.g., fluid on the left side of the partition 428 in FIG. 4) from mixing with the fluid disposed in the chamber 426 downstream of the partition 428. The partition can have a variety of shapes and/or sizes, but in some aspects, is configured to substantially seal to an inner wall of the reservoir 420 such that fluid cannot generally pass between the partition 428 and the inner wall. Thus, if the partition comprises a fluidly impermeable material, fluid will not be exchanged between the upstream portion of the chamber 426 and the downstream portion of the chamber 426. As indicated by the arrow in FIG. 4, the partition 428 can additionally be movable along the direction of fluid flow. Thus, it will be appreciated that as the driving fluid enters the inlet port 420a of the reservoir, pressure is exerted on the upstream surface of the partition 428, thereby forcing the partition 428 to move to the right in FIG. 4 and ejecting the fluid contained within the downstream portion of the chamber from the outlet port 420b. In various aspects, the partition 428 can comprise a fluidly impermeable material that can comprise or be coated with a material for reducing the potential for friction forces between the outer surface of the partition 428 and the inner wall of the reservoir 420. By way of non-limiting example, the partition 428 can comprise a cylindrical disk of polytetrafluoroethylene (PTFE), though it will be appreciated that the partition 428 can be comprised of other shapes and/or materials depending, for example, on the configuration of the inner surface of the reservoir 420.

Figure 5:
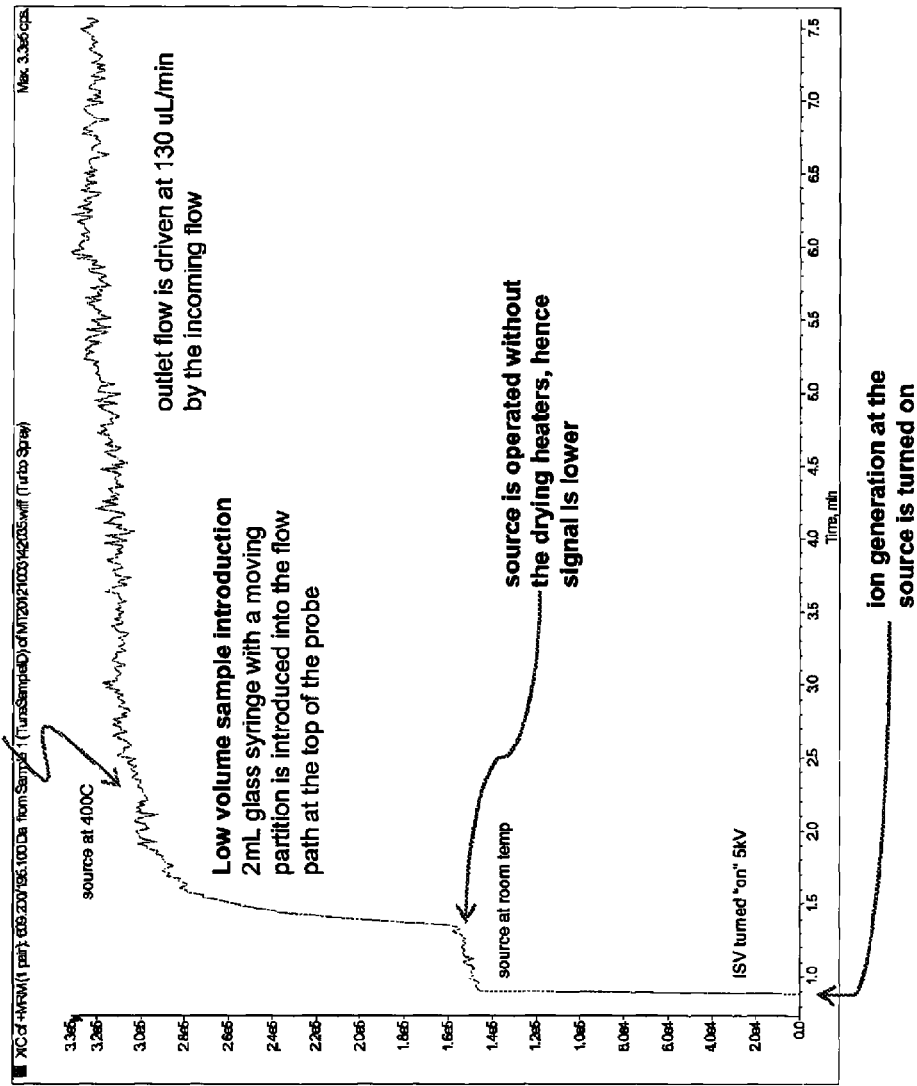
FIG. 5 depicts an exemplary calibrant ion chromatogram demonstrating the stability of an ion signal generated by an exemplary mass spectrometer system in accordance with various aspects of the applicant's teachings.

Use of the exemplary reservoir 420 in a system 200 as shown in FIG. 2 for delivering a calibration fluid to a sample source will now be described with reference to FIG. 5. As shown in FIG. 5, the exemplary ion chromatogram depicts the ion signal detected by an API 4000 QTRAP marketed by AB SCIEX operated in MRM mode for detection of reserpine (positive ion mode, transition 609 Da to 195 Da) when the reservoir 420 is filled with a calibrant comprising a solution of 10 pg/μL reserpine in 50/50/0.1% water/methanol/formic acid. In the exemplary set-up, the chamber 426 of the reservoir 420 (i.e., a 2 mL glass syringe) was filled with the reserpine solution downstream of a PTFE disc and coupled at its outlet end 420b to an ion source probe. The inlet end 420a was then fluidly coupled to a Perkin-Elmer series 200 micro LC pump delivering 50/50 water/methanol mixture to the reservoir 420 at a volumetric flow rate of about 130 μL per minute. In accordance with the present teachings, the volumetric flow rate of the output fluid from the reservoir was driven by the input flow such that the output flow was substantially equal to 130 μL per minute. As shown in FIG. 5, the ion source is turned on so as to generate a first signal (i.e., without the heaters being turned on). After about 1.5 minutes, the desolvation heaters were activated (to about 400° C.) and the detected signal shows an increase as the ion source is heated and ionization efficiency increases. Upon reaching a steady-state temperature for the ion source, the exemplary chromatogram levels off with a relatively stable signal of the reserpine within the calibration fluid (exhibiting a CV of about 2%).

With reference now to FIG. 6, another exemplary embodiment of a reservoir 620 in accordance with various aspects of the present teachings is depicted in detail. The reservoir 620 is substantially similar to the reservoir 420 depicted in FIG. 4, but differs in that the reservoir 620 does not include a partition 428, as shown in FIG. 4. Rather, as the driving fluid is introduced into the inlet port 620a, it can mix with the fluid contained within the fluid chamber 626, such that the outlet fluid comprises a mixture of the driving fluid and the fluid initially contained within the reservoir 620. It will be appreciated in light of the present teachings that the mixing of the fluids can increase over time such that left side of the chamber 626 generally comprises a higher proportion of the driving fluid relative to the right side until all of the fluid initially contained within the chamber 626 is discharged therefrom (e.g., the driving fluid has flushed the reservoir fluid from the chamber 626). It will be appreciated by a person skilled in the art in light of the present teachings that the internal shape of the fluid chamber 626 can alter the mixing and with it the time profile of the composition ratio. By way of example, the chamber 626 could comprise a series of interconnected compartments, with the size of the compartments and their interconnectivity affecting the mixing rate of the driving fluid and the fluid contained within the one or more compartments. Additionally or alternatively, the internal diameter of the fluid chamber 626 can vary along its length (e.g., taper) so as to affect the mixing rate of the input fluid and the fluid initially contained within the chamber 626.

Figure 7:
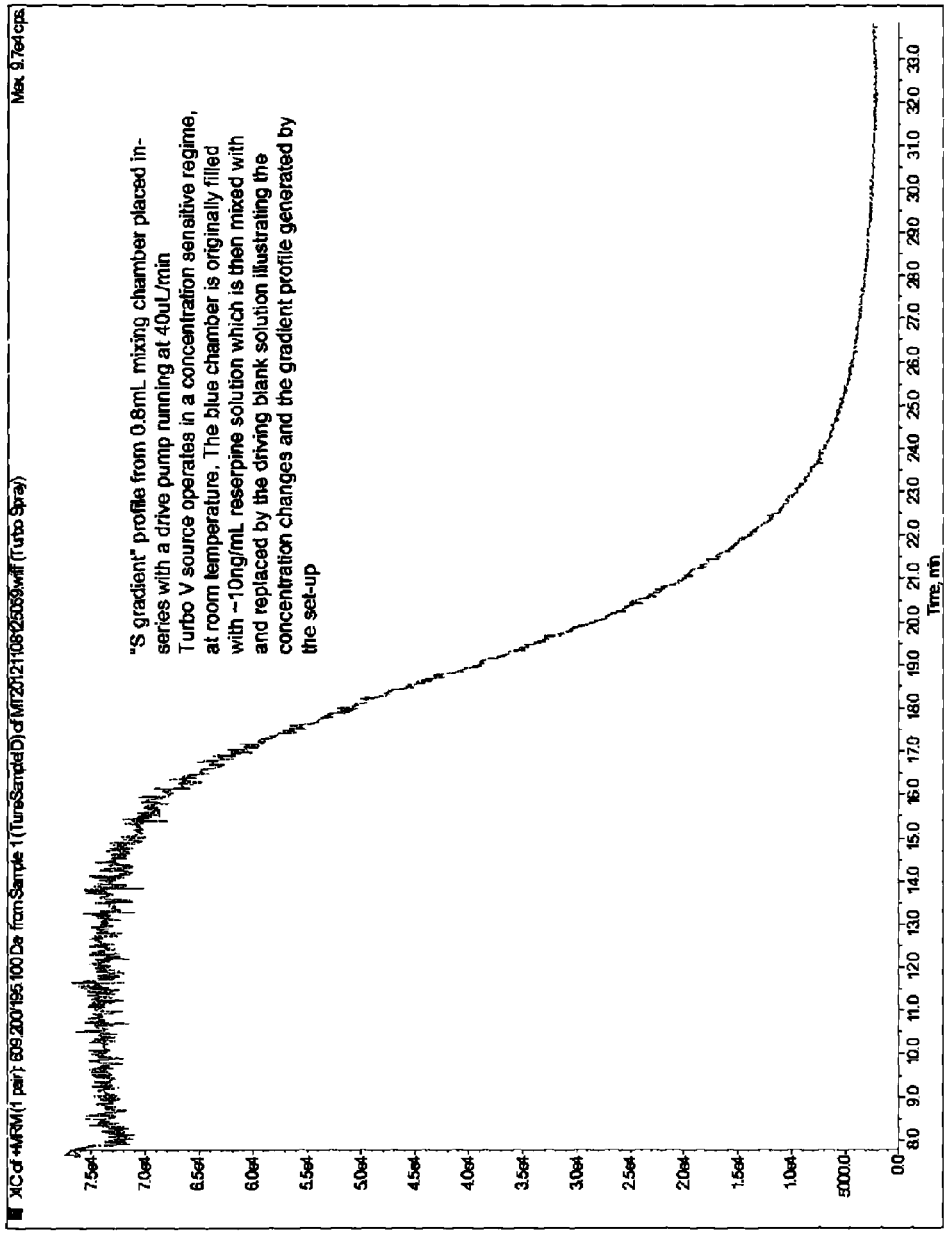
FIG. 7, depicts an ion chromatogram demonstrating the mixing of two liquids within an exemplary reservoir in accordance with various aspects of the applicant's teachings.

With reference now to FIG. 7, demonstration of the use of the exemplary reservoir 620 for mixing the driving fluid with the fluid is contained within the reservoir will now be described. As shown in FIG. 7, the exemplary ion chromatogram depicts the ion signal detected by an API 4000 QTRAP marketed by AB SCIEX operated in MRM mode for detection of reserpine (positive ion mode, transition 609 Da to 195 Da) when the reservoir 620 is filled with a fluid comprising a solution of 10 pg/µL reserpine in 50/50/0.1% water/methanol/formic acid. In the exemplary set-up, the chamber 626 of the reservoir 620 was fluidly coupled at its upstream end to a Perkin-Elmer series 200 micropump delivering 50/50/0.1% water/methanol/formic acid, which generated a volumetric flow rate of about 40 µL per minute and coupled at its outlet end 620b to an ion source probe. In accordance with the present teachings, the volumetric flow rate of the output fluid from the reservoir was driven by the input flow such that the output flow was substantially equal to 40 µL per minute. As shown in FIG. 7, as the driving fluid is introduced into the inlet port 620a, the ion signal indicates that the fluid discharged from the reservoir initially contains a high concentration of reserpine, which decreases over time as the reserpine solution contained within the reservoir is mixed with, and eventually replaced by, the driving blank solution. As will be appreciated by a person skilled in the art, if the driving liquid is a chromatography solution B and the reservoir is initially filled with a chromatography solution A, the reservoir 620 can thus generate a time profile in the composition of its outflow made up of the two chromatography liquids (a so-called S gradient profile), for example, that can be used as the input to the LC column 310 in the system 300 as shown in FIG. 3 to differentially elute various compounds. By way of example, an elution gradient can be generated in the LC column 310 by having the reservoir contain a first solvent initially applied to the LC column at a higher proportion (e.g., 100%) and that is reduced or eliminated as a second solvent replaces the first solvent within the reservoir.

Figure 8A:
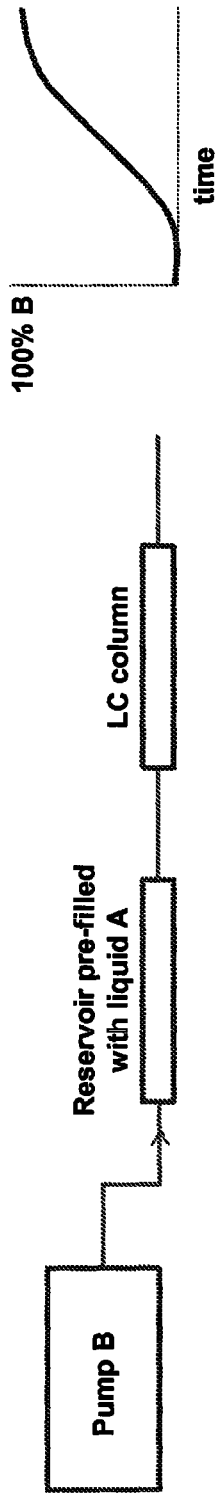
FIG. 8A, in a schematic diagram, illustrates an exemplary fluid flow pathway containing a reservoir in accordance with various aspects of the applicant's teachings and a schematic ion chromatogram demonstrating the mixing of two liquids within the reservoir.
Figure 8B:
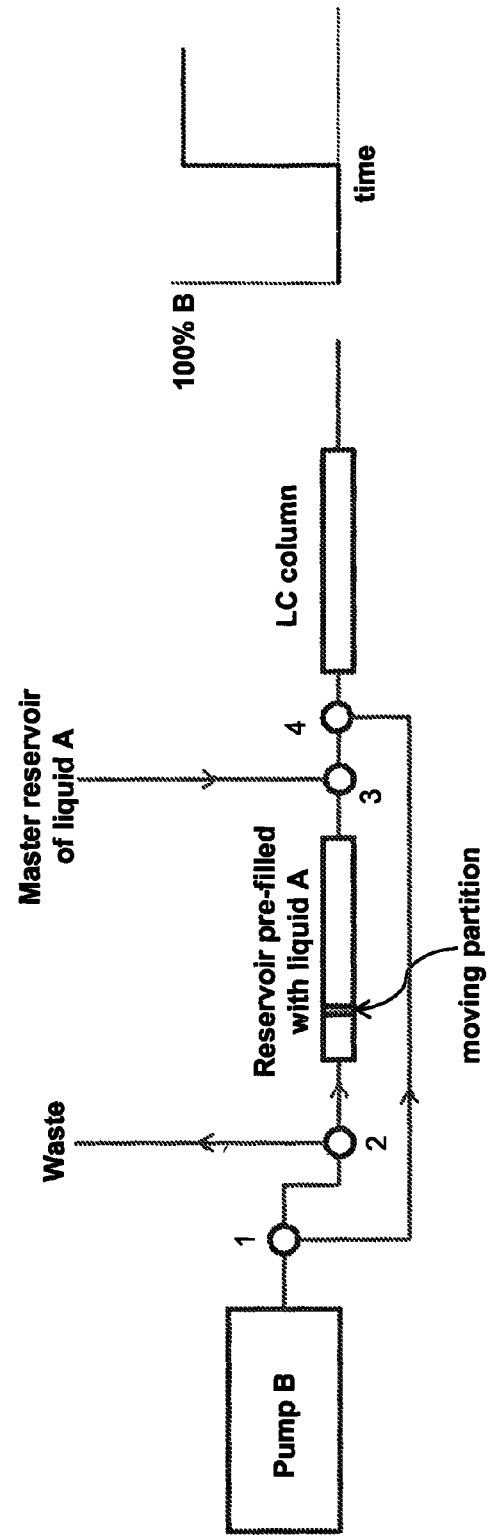
FIG. 8B, in a schematic diagram, illustrates an exemplary fluid flow pathway containing a reservoir in accordance with various aspects of the applicant's teachings having a refill capability and another schematic ion chromatogram demonstrating a stepwise elution gradient.

With reference now to FIGS. 8A-B, exemplary systems for fluidly coupling the reservoir(s) (e.g., several reservoirs can be coupled in series or in parallel, each containing the same or different fluids) to a fluid flow pathway in accordance with various aspects of the present teachings is depicted. FIG. 8A, for example, depicts the use of the reservoir substantially as described with reference to FIG. 7 for providing an exemplary S-gradient elution gradient profile to an LC column. That is, the reservoir can be pre-filled with Solvent A and disposed between the LC column and an HPLC pump(s) coupled to a reservoir containing Solvent B. As Solvent B is pumped into the reservoir of FIG. 8A, the proportion of Solvent B in the resulting mobile phase applied to the LC column increases over time as depicted schematically until the reservoir is emptied of Solvent A. Thus, a single HPLC pump can used to both pump and/or mix the solvents applied to the LC column, thereby eliminating one of the high pressure LC pumps and mixing element typically used to drive the mobile phase in known systems. It will be appreciated in light of the present teachings that one or more reservoirs can be placed in series or in parallel (e.g., via a bypass) with the reservoir depicted in FIG. 8A to enable the mixing of more than two components, for example.

With reference now to FIG. 8B, the use of a reservoir having a movable partition is depicted schematically for generating a stepwise profile in the mobile phase. That is, the partition can substantially prevent the driving fluid from mixing with the fluid contained within the reservoir such that the fluid discharged from the reservoir has the same composition as that initially contained therein. Thus, the mobile phase initially applied to the LC column comprises 100% Solvent A. After a pre-determined time, for example, one or more valves can be actuated, for example, such that Solvent B is diverted into a bypass conduit and such that the reservoir is fluidly decoupled from the LC column. As shown in FIG. 8B, the mobile phase applied to the LC column can thus be switched in stepwise fashion to 100% Solvent B.

It will be appreciated that any number and configuration of valve mechanisms and bypass conduits can be used in accordance with the present teachings. For example, FIG. 8B depicts an exemplary valve manifold for refilling the reservoir. It will be appreciate that though the valve manifold of FIG. 8B is shown in use with a reservoir having a moving partition, the present teachings can also be utilized to re-fill, for example, a reservoir that does not include such a partition. In the exemplary fluid pathway depicted in FIG. 8B, for example, two three-way valves 1, 2 are disposed upstream of the reservoir (i.e., between the pump and the reservoir) and two three-way valves 3, 4 are disposed downstream of the reservoir (i.e., between the reservoir and the LC column). To bypass and/or re-fill the reservoir, valves 1 and 4 can be actuated such that the fluid from pump B bypasses the reservoir, while valves 2 and 3 can be actuated to refill the reservoir from a master source of liquid A (e.g., the waste fluid is driven to a waste reservoir as liquid A refills the reservoir). In some aspects, the refill can be performed at low pressure and can, for example, be achieved by a gravity fed path or by a low-cost, low pressure pump. Upon re-filling the reservoir, the valves can then be actuated such that fluid again is delivered by Pump B into the inlet end of the reservoir. Though four three-way valves are depicted in FIG. 8B, it will be appreciated that two four-way valves, for example, could be used instead to divert the driving fluid into the bypass conduit and/or refill the reservoir while removing waste.

With reference now to FIG. 9, another exemplary reservoir 920 in various aspects of the present teachings is depicted. Like the exemplary reservoir 420 of FIG. 4, the reservoir 920 comprises a inlet port 920a for receiving a driving fluid, a fluid chamber 926 containing a fluid to be discharged from an outlet port 920b of the reservoir 920, and a partition 928 segregating the driving fluid from the fluid initially contained in the chamber 926. The partition 928 differs, however, in that the partition 928 comprises a flexible bladder that is configured to expand as the driving fluid is flowed therein. As will be appreciated by a person skilled in the art in light of the present teachings, as the bladder 928 expands, the pressure within the reservoir 920 will increase, thereby driving the fluid contained within the fluid chamber 926 out of the outlet port 920b. It will further be appreciated that the partition can comprise a variety of materials, but generally can be fluid-impermeable and configured to expand and/or stretch upon receiving fluid through the inlet port 920a. By way non-limiting example, the partition 928 can comprise EPDM (ethylene propylene diene monomer rubber), neoprene, latex rubber, fluoroelastomers (e.g., FPM/FKM), and perfluoroelastomers (FFPM/FKM).

The section headings used herein are for organizational purposes only and are not to be construed as limiting. While the applicant's teachings are described in conjunction with various embodiments, it is not intended that the applicant's teachings be limited to such embodiments. On the contrary, the applicant's teachings encompass various alternatives, modifications, and equivalents, as will be appreciated by those of skill in the art.

The invention claimed is:

1. A system for delivering fluid to a mass spectrometry system, the system comprising:
   a single displacement pump; and
   a reservoir comprising an inlet port configured to receive a first fluid driven by said pump and an outlet port configured to expel an output fluid of different composition than said first fluid, the reservoir pre-filled with a second fluid, wherein the outlet port is configured to fluidly couple to an ion source of a mass spectrometry system;
   the single displacement pump providing a flow of the first fluid to the pre-filled reservoir through the inlet port, the flow generated by the single displacement pump discharges the output fluid contained within the reservoir at substantially the same volumetric flow rate as the flow entering the inlet port of the reservoir;
   wherein the flow rate of the output fluid is between about 10 µL/min to about 20 mL/min.

2. The system of claim 1, further comprising a liquid chromatography (LC) column fluidly coupled to the pump.

3. The system of claim 2, wherein the LC column is disposed between the pump and the reservoir and wherein the first fluid comprises an eluent from the LC column and the output fluid comprises a steady state flow of calibration fluid.

4. The system of claim 2, wherein the reservoir is disposed between the pump and the LC column.

5. The system of claim 4, wherein the second fluid has a different composition than the first fluid and the output fluid, and wherein the first fluid comprises a first LC solvent and the second fluid comprises a second LC solvent, and wherein the output fluid comprises a mixture of the first and second LC solvents.

6. The system of claim 1, further comprising a fluid flow pathway extending between the pump and the ion source, wherein said reservoir is configured to removably couple to said fluid flow pathway, wherein the LC column is temporarily replaced by the reservoir.

7. The system of claim 1, wherein the reservoir further comprises a liquid impermeable partition disposed between the inlet port and the outlet port.

8. The system of claim 7, wherein the partition is movable along the axis of the reservoir, along the direction of the fluid flow, ejecting the fluid from the outlet port.

9. The system of claim 6, further comprising a second reservoir disposed downstream of the first reservoir in the fluid flow pathway, wherein an inlet port of the second reservoir is configured to receive the output fluid of the first reservoir.

10. The system of claim 6, further comprising a bypass conduit extending from a first end coupled to the fluid flow pathway upstream from the reservoir to a second end coupled to the fluid flow pathway downstream from the reservoir, wherein the bypass is configured to divert the first fluid flow from the reservoir.

11. A method for delivering fluid to a mass spectrometry system, the method comprising:
    operating a single displacement pump to introduce a first fluid into an inlet port of a reservoir, said reservoir pre-filled with a second fluid different than said first fluid;
    discharging an output fluid from an outlet port of said reservoir at substantially the same volume flow rate as the flow entering the inlet port, wherein said output fluid is of a different composition from said first fluid and the flow rate of the output fluid is between about 10 µL/min to about 20 mL/min; and
    delivering a sample fluid to be ionized to an ion source of a mass spectrometer.

12. The method of claim 11, wherein said pump introduces a solvent into a liquid chromatography (LC) column, wherein the pump, LC column, reservoir, and ion source being fluidly coupled via a fluid flow pathway.

13. The method of claim 12, wherein the LC column is disposed in the fluid flow pathway between the pump and the reservoir.

14. The method of claim 13, wherein the first fluid comprises an eluent from the LC column and wherein said second fluid, said output fluid, and said sample fluid comprise a calibration fluid.

15. The method of claim 12, wherein the reservoir is disposed in the fluid flow pathway between the pump and the LC column.

16. The method of claim 15, wherein the first fluid comprises a first LC solvent and the second fluid comprises a second LC solvent, and wherein the solvent introduced into the LC column comprises the output fluid discharged from the reservoir.

17. The method of claim 16, wherein the output fluid discharged from the reservoir is configured to provide a gradient elution of the LC column and consists of the second LC solvent during a first time duration.

18. The method of claim 17, wherein the output fluid discharged from the reservoir is configured to provide a gradient elution of the LC column and comprises a mixture of the first and second LC solvents during a second time duration after the first time duration.

19. The system of claim 1, wherein the output flow is discharged into a nebulizing gas flow, the nebulizing gas flow between about 0.1 L/min and about 20 L/min.

20. The system of claim 2, further comprising a fluid flow pathway extending between the pump and the ion source, wherein said reservoir is configured to removably couple to said fluid flow pathway upstream of an LC column to provide an elution gradient.

* * * * *